(12) United States Patent
Yoshino et al.

(10) Patent No.: US 9,033,503 B2
(45) Date of Patent: May 19, 2015

(54) FUNDUS PHOTOGRAPHING APPARATUS

(75) Inventors: Masayuki Yoshino, Gamagori (JP); Yusuke Ando, Gamagori (JP)

(73) Assignee: NIDEK CO., LTD., Gamagori-shi (JP)

( * ) Notice: Subject to any disclaimer, the term of this patent is extended or adjusted under 35 U.S.C. 154(b) by 29 days.

(21) Appl. No.: 13/427,345

(22) Filed: Mar. 22, 2012

(65) Prior Publication Data

US 2012/0242955 A1 Sep. 27, 2012

(30) Foreign Application Priority Data

Mar. 22, 2011 (JP) ................................. 2011-062621

(51) Int. Cl.
  *A61B 3/14* (2006.01)
  *A61B 3/10* (2006.01)
  *A61B 3/00* (2006.01)
  *A61B 3/15* (2006.01)

(52) U.S. Cl.
  CPC ............... *A61B 3/152* (2013.01); *A61B 3/0091* (2013.01)

(58) Field of Classification Search
  CPC ........ A61B 3/152; A61B 3/103; A61B 3/113; A61B 3/1225; A61B 3/14; A61B 3/1015; A61B 3/145
  USPC ......... 351/208, 200, 205, 210, 221, 246, 206, 351/211
  See application file for complete search history.

(56) References Cited

U.S. PATENT DOCUMENTS

| 7,771,050 | B2* | 8/2010 | Honda et al. ................... 351/208 |
| 2002/0127010 | A1* | 9/2002 | Ohtsuka ........................... 396/18 |
| 2005/0068496 | A1 | 3/2005 | Ichikawa | |
| 2006/0114412 | A1* | 6/2006 | Tawada .......................... 351/206 |
| 2009/0190092 | A1* | 7/2009 | Tsukada et al. ................ 351/208 |

FOREIGN PATENT DOCUMENTS

| EP | 2138093 A1 | 12/2009 |
| JP | A-6-46999 | 2/1994 |
| JP | A-2005-95450 | 4/2005 |
| JP | A-2006-116091 | 5/2006 |
| JP | 2007-202724 A | 8/2007 |

* cited by examiner

*Primary Examiner* — Dawayne A Pinkney
(74) *Attorney, Agent, or Firm* — Oliff PLC

(57) ABSTRACT

A fundus photographing apparatus for photographing a fundus of an examinee's eye includes: a photographing part including a photographing optical system for photographing the fundus; a mechanism for moving the photographing part; a presenting part for presenting a fixation target to the eye; an alignment detecting optical system including a light receiving element to detect an alignment state of the photographing part; and a setting part for setting an alignment completion position in a back and forth direction of the photographing part relative to the eye based on the detected alignment state. The alignment completion position includes a first alignment completion position information to be set when an optical axis of the photographing part is in a predetermined range relative to a corneal vertex of the eye and a second alignment completion position information to be set when the optical axis is apart from the predetermined range.

7 Claims, 5 Drawing Sheets

FUNDUS PHOTOGRAPHING APPARATUS

CROSS-REFERENCE TO RELATED APPLICATIONS

This application is based upon and claims the benefit of priority from the prior Japanese Patent Application No. 2011-62621, filed on Mar. 22, 2011, the entire contents of which are incorporated herein by reference.

TECHNICAL FIELD

The present invention relates to a fundus photographing apparatus for photographing a fundus of an examinee's eye.

BACKGROUND ART

When a conventional fundus photographing apparatus such as a fundus camera is to be aligned with an examinee's eye induced to look at a predetermined fixation point, alignment for observation of an anterior segment is performed so that an alignment index and a reticle formed in a predetermined position on a screen of a display monitor are placed in a predetermined relationship. Further, alignment for observation of a fundus is generally performed so that a reticle formed at a predetermined point on the screen of the display monitor coincides with a corneal luminescent spot (so-called a working dot) while referring to the corneal luminescent spot observable together with a fundus observation image (see Patent document 1).

RELATED ART DOCUMENTS

Patent Documents

Patent Document 1: JP 2006-116091 A

DISCLOSURE OF THE INVENTION

Problems to be Solved by the Invention

Meanwhile, when a peripheral region of a fundus is to be photographed (peripheral photographing), an examinee's eye is guided for peripheral fixation and thus the visual axis of the eye is displaced from a photographing optical axis. Even when the alignment is performed so that the reticle coincides with the alignment index (corneal luminescent spot), illumination unevenness is caused on an image of the photographed fundus. In some cases, therefore, a good fundus image could not be obtained. When the peripheral photographing is to be performed, this photographing may be conducted with the photographing optical axis slightly displaced from a corneal vertex. Such photographing with the photographing optical axis displaced from the corneal vertex can prevent illumination unevenness, however, flares are apt to occur. Further, stereo photographing with a corneal vertex and a photographing optical axis displaced from each other is likely to cause the same problem.

The present invention has an object to provide a fundus photographing apparatus capable of restraining the occurrence of flares when photographing is to be performed while a photographing optical axis is in a displaced state from a corneal vertex.

Means of Solving the Problems

To achieve the above object, one aspect of the invention provides a fundus photographing apparatus for photographing a fundus of an examinee's eye, the apparatus comprising: a photographing part including a photographing optical system for photographing the fundus of the eye; a moving mechanism for relatively moving the photographing part with respect to the eye; a fixation target presenting part for presenting a fixation target to the eye; an alignment detecting optical system including a light receiving element to detect an alignment state of the photographing part with respect to the eye in fixation; and an alignment completion position setting part for setting an alignment completion position in a back and forth direction of the photographing part with respect to the eye based on the alignment state detected by the alignment detecting optical system, the alignment completion position including a first alignment completion position information to be set when a photographing optical axis of the photographing part is in a predetermined range with respect to a position of a corneal vertex of the eye and a second alignment completion position information to be set when the photographing optical axis is in a position apart from the predetermined range with respect to the corneal vertex position.

Effects of the Invention

According to the invention, a fundus photographing apparatus for photographing a fundus can prevent the occurrence of flares when photographing is performed while a photographing optical axis is off a corneal vertex.

MODE FOR CARRYING OUT THE INVENTION

Figure 1:
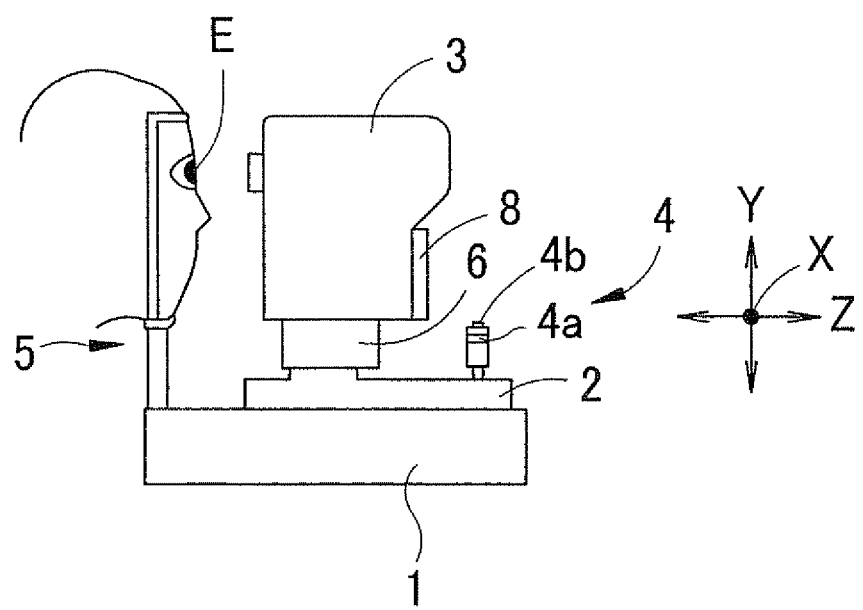
FIG. 1 is a schematic external view of a fundus camera of an embodiment.

A preferred embodiment according to the present invention will be explained referring to the accompanying drawings. FIG. 1 is a perspective external view of a fundus camera of the present embodiment. This fundus camera includes a base 1, a movable table 2 that can be moved relative to the base 1 in a right and left direction (X direction) and a back and forth (working distance) direction (Z direction), a photographing part (main unit) 3 provided to be movable relative to the movable table 2 in a three-dimensional direction and containing optical systems mentioned later, and a head supporting unit 5 fixed to the base 1 to support the face (head) of an examinee.

The present apparatus further includes an automatic moving mechanism having an electric motor to relatively move the photographing part 3 with respect to an examinee's eye. To be more specific, the photographing part 3 is moved in the right and left direction (X direction), an up and down direction (Y direction), and the back and forth direction (Z direction) with respect to an examinee's eye E by a motor-operated XYZ drive part 6 provided on the movable table 2. The present apparatus further includes a manual moving mechanism to relatively move the photographing part 3 with respect to the examinee's eye by operation of an operating member (joystick 4). More specifically, there is provided a sliding mechanism not shown to slide the movable table 2 in the X-Z direction on the base 1. When the joystick 4 is operated, the movable table 2 is slid in the X-Z direction on the base 1. Furthermore, when a rotation knob 4a is rotated, the XYZ drive part 6 is Y-driven to thereby move the photographing part 3 in the up and down direction. On an examiner side of the photographing part 3, a monitor 8 for displaying a fundus observation image, a fundus photographing image, an anterior-segment observation image, etc.

Figure 2A:
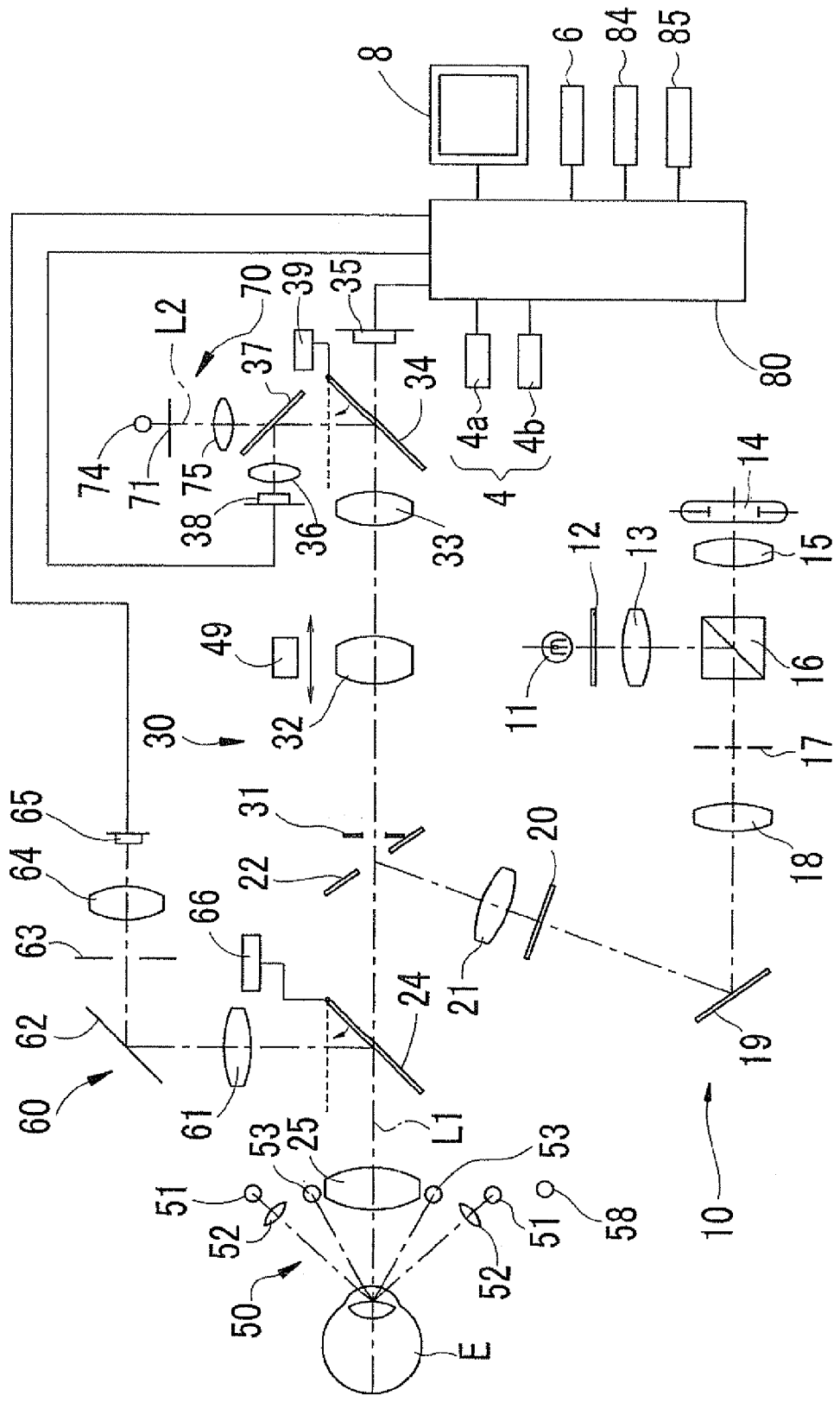
FIG. 2A is a diagram showing optical systems and a control system of the fundus camera of the embodiment.

FIG. 2A is a schematic configuration view showing optical systems and a control system contained in the photographing part 3. In FIG. 2A, the optical systems roughly include an illumination optical system 10, a fundus observation-photographing optical system 30 for photographing a fundus image of the examinee's eye, an alignment index projecting optical system 50, an anterior-segment observation optical system 60, and a fixation target presenting optical system 70.

<Illumination Optical System>

The illumination optical system 10 has an observation illumination optical system and a photographing illumination optical system. The photographing illumination optical system includes a photographing light source 14 such as a flash lamp, a condenser lens 15, a ring slit 17, a relay lens 18, a mirror 19, a black point plate 20 having a black point at a center thereof, a relay lens 21, a perforated mirror 22, and an objective lens 25. The observation illumination optical system includes a light source 11 such as a halogen lamp or the like, an infrared filter 12 that transmits near infrared light having a wavelength of 750 nm or more, a condenser lens 13, a dichroic mirror 16, and the optical system from the ring slit 17 to the objective lens 25. The dichroic mirror 16 has the property of reflecting infrared light emitted from the light source 11 while transmitting visible light emitted from the photographing light source 14.

<Fundus Observation and Fundus Photographing Optical System>

The fundus observation-photographing optical system 30 includes the objective lens 25, a photographing diaphragm 31 located near an aperture of the perforated mirror 22, a focusing lens 32 movable in a photographing optical axis direction, an imaging lens 33, and a flip-up mirror 34 that is inserted in or removed from an optical path by an inserting/removing mechanism 39 during fundus photographing. It is to be noted that the photographing optical system and the fundus observation optical system share the optical components from the objective lens 25 to the imaging lens 33. The photographing diaphragm 31 is placed in a position substantially conjugate with a pupil of the eye E with respect to the objective lens 25. The focusing lens 32 is moved in the photographing optical axis direction by a moving mechanism 49 provided with a motor. A two-dimensional imaging element 35 for photographing is sensitive to light in a visible region. On an optical path in a reflecting direction of the flip-up mirror 34, a dichroic mirror 37 having the property of transmitting visible light is placed and further a relay lens 36 and a two-dimensional imaging element 38 for observation sensitive to light in an infrared region are arranged.

An optical path splitting member is obliquely placed between the objective lens 25 and the perforated mirror 22. This optical path splitting member in the present embodiment is a dichroic mirror (wavelength selecting mirror) 24. The dichroic mirror 24 has the property of reflecting light of wavelengths (Center wavelength: 940 nm) of the alignment index projecting optical system 50 and an anterior-segment illumination light source 58 while transmitting light of a wavelength of 900 nm or less including wavelengths (Center wavelength: 880 nm) of the illumination light source for fundus observation. During fundus photographing using the visible light, the dichroic mirror 24 is flipped up in sync with the flip-up mirror 34 by an inserting/removing mechanism 66 so that the dichroic mirror 24 is put out of the optical path. The inserting/removing mechanism 66 consists of for example a solenoid, a mirror, and others.

Light emitted from the observation light source 11 is converted to infrared light by the infrared filter 12, passes through the condenser lens 13 and then is reflected by the dichroic mirror 16 to illuminate the ring slit 17. The light having passed through the ring slit 17 reaches the perforated mirror 22 via the relay lens 18, the mirror 19, the black point plate 20, and the relay lens 21. The light reflected by the perforated mirror 22 passes through the dichroic mirror 24 and converges once near the pupil of the eye E through the objective lens 25, and then disperses to illuminate the fundus of the eye.

The reflection light from the fundus passes through the objective lens 25, the dichroic mirror 24, the aperture of the perforated mirror 22, the photographing diaphragm 31, the focusing lens 32, the imaging lens 33, the flip-up mirror 34, the dichroic mirror 37, and the relay lens 36, and then forms an image on the imaging element 38. A signal outputted from the imaging element 38 is inputted to the controller 80. Based on the input signal, the controller 80 displays a fundus observation image of the examinee's eye on the monitor 8. Further, the light emitted from the photographing light source 14 passes through the condenser lens 15 and the dichroic mirror 16, and travels along the same optical path as that of the illumination light for fundus observation. The fundus is thus illuminated with visible light. The reflection light from the fundus passes through the objective lens 25, the aperture of the perforated mirror 22, the photographing diaphragm 31, the focusing lens 32, and the imaging lens 33, and then forms an image on the two-dimensional imaging element 35.

<Alignment Index Projecting Optical System>

Figure 2B:
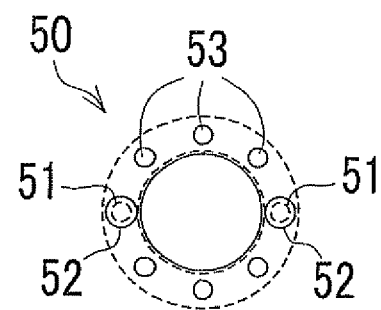
FIG. 2B is a diagram of an alignment index projecting optical system shown in FIG. 2A, seen from an photographing optical axis direction thereof.

The alignment index projecting optical system 50 for projecting index light for alignment includes a plurality of infrared light sources placed on a concentric circle centered on the optical axis L1 and at angular intervals of 45° as shown in FIG. 2B. This optical system 50 further includes a first index projecting optical system (0° and 180°) having infrared light sources 51 and collimating lenses 52 placed to be horizontally symmetric about a vertical plane passing through the optical axis L1 and a second index projecting optical system having six infrared light sources 53 arranged in positions different from the first index projecting optical system. In the present embodiment, the first index projecting optical system is configured to project infinite indexes to a cornea of the eye E from right and left directions. Further, the second index projecting optical system is configured to project finite indexes to the cornea of the eye E from up and down directions or oblique directions. FIG. 2A shows, for convenience, the first index projecting optical system (0° and 180°) and only a part of the second index projecting optical system (45° and 135°).

<Anterior-Segment Observation Optical System>

The anterior-segment observation (photographing) optical system 60 for imaging the anterior segment of the examinee's eye is provided, on a reflecting side of the dichroic mirror 24, with a field lens 61, a mirror 62, a diaphragm 63, a relay lens 64, and a two-dimensional imaging element (light receiving element) 65 being sensitive to light in an infrared region. The two-dimensional imaging element 65 is also used as an imaging device for detecting alignment indexes. This imaging element 65 images the anterior segment illuminated by the anterior-segment illumination light source 58 that emits infrared light of a center wavelength of 940 nm and the alignment index projected to the examinee's eye. The light from the anterior segment illuminated by the anterior-segment illumination light source 58 passes through the objective lens 25, the dichroic mirror 24, and the optical system from the field lens 61 to the relay lens 64, and then falls on the two-dimensional imaging element 65. The alignment light emitted from the light source of the alignment index projecting optical system 50 is projected to the cornea of the examinee's eye. A resultant corneal reflection image is received by (projected to) the two-dimensional imaging element 65 via the components from the objective lens 25 to the relay lens 64. A signal outputted from the two-dimensional imaging element 65 is inputted to the controller 80 and thereby an anterior segment image imaged by this imaging element 65 is displayed on the monitor 8. The anterior-segment observation optical system 60 also uses an alignment detection optical system including a light receiving element (the two-dimensional imaging element 65) to detect misalignment of the photographing part 3 with respect to the examinee's eye.

<Fixation Target Presenting Optical System>

The fixation target presenting optical system 70 for presenting a fixation target which the examinee's eye is induced to look at is provided with a red light source 74, a light shielding plate 71 formed with a hole, and a relay lens 75, and includes, via the dichroic mirror 37, the optical path extending from the flip-up mirror 34 to the objective lens 25 in the observation optical system 30. The fixation target presenting optical system 70 has a configuration (not shown) to change a presenting position of a fixation target, whereby directing the visual line of the examinee's eye in a predetermined direction (see e.g. JP 2005-95450 A). Accordingly, peripheral photographing can also be performed. In the present embodiment, the light shielding plate 71 illuminated from behind by the light source 74 forms a fixation target (a fixation lamp). The light from the fixation target passes through the relay lens 75, the dichroic mirror 37, the flip-up mirror 34, the imaging lens 33, the focusing lens 32, the perforated mirror 22, the dichroic mirror 24, and the objective lens 25, then converges on the fundus of the examinee's eye. The examinee visually recognizes the light from the hole 71 as a fixation target.

<Controller>

The two-dimensional imaging elements 65, 38, and 35 are connected to the controller 80. This controller 80 detects the alignment indexes from the anterior segment image imaged by the two-dimensional imaging element 65 and processes the detected alignment indexes. Further, the controller 80 is connected to the monitor 8 to control display of the monitor 8. To the controller 80, additionally, there are connected the XYZ drive part 6, the moving mechanism 49, the inserting/removing mechanism 39, the rotation knob 4a, the photographing switch 4b, a switch unit 84 including various switches, a memory 85 serving as a storage device, and each light source and others. Herein, the controller 80 detects misalignment of the photographing part 3 with respect to the examinee's eye based on the light receiving signal outputted from the imaging element (light receiving element) 65 and outputs a drive signal to the XYZ drive part 6 based on the detection result.

Figure 3A:
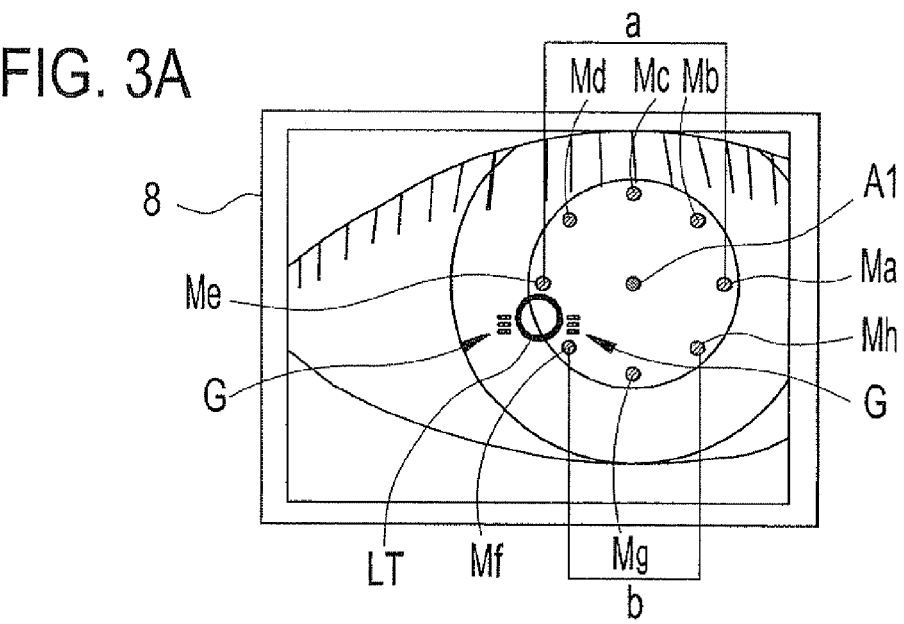
FIGS. 3A to 3C are diagram showing alignment states with respect to an anterior segment image displayed on a monitor.
Figure 3B:
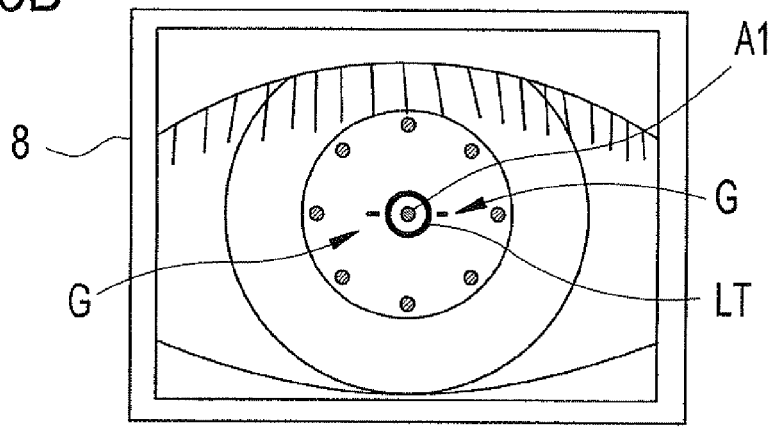
Figure 3C:
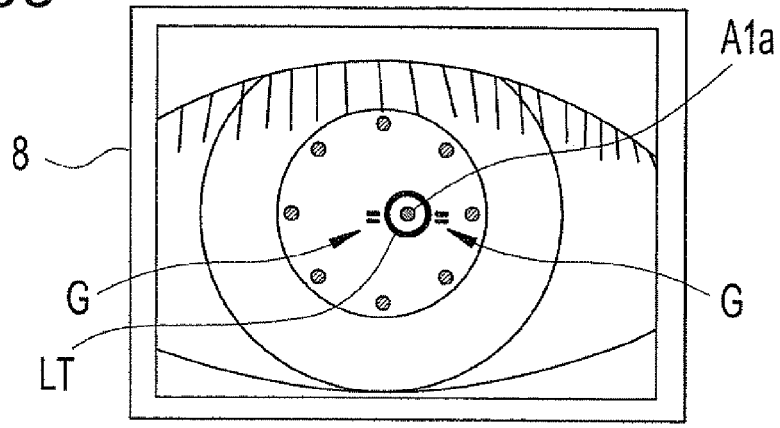
Figure 4:
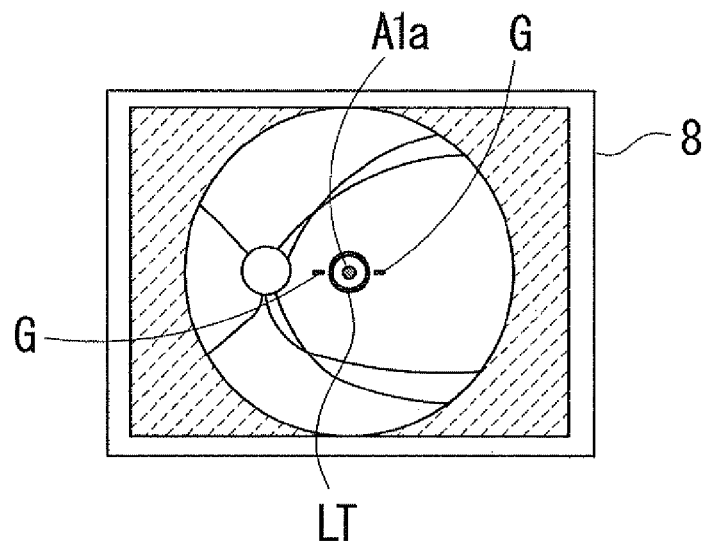
FIG. 4 is a diagram showing a monitor on which a fundus image is displayed.

FIGS. 3A to 3C show examples of an anterior-segment observation screen displayed on the monitor 8. FIG. 4 shows an example of a fundus observation screen displayed on the monitor 8. The controller 80 electronically creates and displays a reticle (an alignment mark) LT as an alignment reference at a predetermined position on the screen of the monitor 8. The controller 80 also electronically creates and displays an alignment index A1 on the screen of the monitor 8 so that a relative distance between the alignment index A1 and the reticle LT changes based on the detected misalignment in the XY direction. Further, the controller 80 displays indicators G representing misalignment in the Z direction and increases/decreases the number of indicators G based on the detected misalignment in the Z direction. In the present embodiment, an alignment completion position (an alignment reference position) of the photographing part 3 with respect to the examinee's eye E in the Z direction is changed according to the position of the photographing optical axis (optical axis L1) of the photographing part 3 with respect to the eye E. In the present embodiment, consequently, the alignment completion position in the Z direction is changed according to the misalignment in the XY direction.

Figure 5:
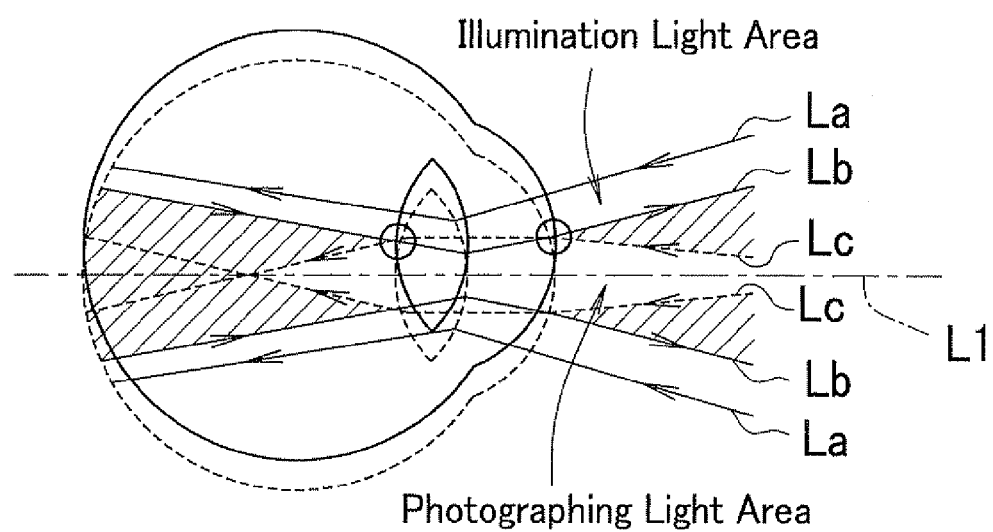
FIG. 5 is a schematic diagram showing an illumination light area and a photographing light area of the fundus camera with respect to an examinee's eye.

Next, a phenomenon that flares are caused by displacement of the photographing optical axis to an eye is explained referring to FIG. 5 showing a schematic optical-path diagram. The examinee's eye indicated by a dotted line represents a state where the photographing optical axis L1 passes through a corneal vertex (a position of a cornea that is a most anterior surface with respect to the photographing optical axis). Further, the examinee's eye indicated with a solid line represents a state of the corneal vertex relatively displaced from the photographing optical axis L1. The aforementioned illumination light area formed by the illumination optical system, near the pupil, is set in the vicinity of the pupil of the examinee's eye. On the other hand, the photographing light area formed by the fundus observation-photographing optical system is set in the vicinity of the center of the pupil. As illustrated in the figure, the illumination light area is located between the illumination light La and the illumination light Lb indicated by solid lines and the photographing light area is formed by the photographing light Lc indicated by the dotted lines.

When the photographing part (herein, the fundus observation-photographing optical system) is designed to ensure a required working distance to an examinee's eye and the photographing optical axis L1 is located at the corneal vertex of the eye, an area (a shaded portion in the figure) in which the illumination light area and the photographing light overlap each other is configured not to lie on the cornea and the lens (posterior surface). The working distance indicates a proper distance in the Z direction of the photographing part with respect to the examinee's eye. In the present embodiment, it represents an optically determined distance from the corneal vertex of the examinee's eye to the objective lens 25. On the other hand, when the photographing optical axis L1 is located in a displaced position from the corneal vertex of the examinee's eye while the working distance is ensured, an overlapping area of the illumination light area and the photographing light area passes the cornea and the posterior surface of the lens, resulting in that flares (noise light) are liable to occur (a portion indicated by a circle in the figure). In the present embodiment, therefore, when fundus photographing is to be performed while the photographing optical axis L1 is off the corneal vertex of the examinee's eye, a distance at which the overlapping area of the illumination light area and the photographing light is displaced from at least the cornea (a distance at which the occurrence of flares due to the reflection light from the cornea is restrained) is set as a new working distance. In the case where the photographing optical axis L1 is put in the position displaced from the corneal vertex, the new working distance may be set for example in a manner such that a model eye used in designing the optical system of the fundus camera is utilized, and the new working distance, at which the occurrence of flares is restrained in a position in which the photographing optical axis is displaced from the corneal vertex, is determined in advance by calculation based on existing optical design information. Such new working distance can be set to stepwise or continuously change according to an amount of displacement of the photographing optical axis from the corneal vertex. FIG. 5 shows a state where the photographing optical axis is displaced relatively parallel with the examinee's eye. As another example, the above concept is also basically applicable to even the case where the visual axis of the examinee's eye is inclined to the photographing optical axis by the fixation target for peripheral photographing and others. In the present embodiment, the meaning that the photographing optical axis L1 is displaced from the corneal vertex does not indicate that the photographing optical axis L1 is strictly deviated from the corneal vertex, and includes a state where the photographing optical axis L1 is displaced beyond a predetermined range from the corneal vertex.

Alignment detection in the Z direction (working distance detection) in the present embodiment is determined from an alignment deviation amount in the Z direction obtained by comparing image ratios of an image interval between a pair of infinite index images detected by the two-dimensional imaging element 65 and an image interval between a pair of finite index images. Such alignment detection in the Z direction is achieved by utilizing the characteristics that when the photographing part is displaced in the working distance, the image interval between the pair of infinite index images projected to the examinee's eye changes little, whereas the image interval between the pair of finite index images changes, and determining the alignment deviation amount in the working distance with respect to the examinee's eye (for the details, refer to JP 6(1994)-46999 A). In such a Z-direction alignment detection method, each alignment luminescent spot (index) remains unchanged even when the photographing optical axis is displaced from the corneal vertex in the up and down, right and left directions. In the present embodiment, therefore, when the working distance to be set is changed according to the position of the photographing optical axis with respect to the examinee's eye (cornea), it is only necessary to set various values of the image ratio (a ratio between the interval between the infinite index images and the interval between the finite index images) assumed as the alignment completion position in the Z direction according to the position of the photographing optical axis with respect to the examinee's eye. To be more specific, the image ratio assumed as the alignment completion position in the Z direction while the photographing optical axis is in a displaced position from the corneal vertex is set as a different value from the image ratio assumed as the alignment completion position in the Z direction at which the photographing optical axis is in an aligned position with the corneal vertex. This setting information is stored in advance in the memory 85 in association with the displacement amount of the photographing optical axis from the corneal vertex.

Operations of the fundus camera configured as above will be explained below. The following explanation is given to an example of stereo photographing performed by displacing the photographing optical axis rightward and leftward by a predetermined amount from the corneal vertex of the examinee's eye. When powered on, the controller 80 executes initialization of a presenting position of a fixation target, an alignment reference position, a reticle displaying position, etc. The presenting position of the fixation target can be changed with a predetermined switch for changing a visual line direction provided on the switch unit 84.

An examiner first requests the examinee to put his/her head on the head supporting unit 5. In an initial stage, the dichroic mirror 24 is located on the optical path of the photographing optical system 30 and the anterior segment image imaged by the two-dimensional imaging element 65 is displayed on the monitor 85. The examiner moves the photographing part 3 in right and left, up and down directions by operation of the joystick 4 so that the anterior segment image appears on the monitor 8. When the anterior segment image appears on the monitor 8, eight index images Ma to Mh come appear as shown in FIG. 3A.

When the alignment index images projected to the cornea of the examinee's eye are detected by the two-dimensional imaging element 65 as described above, the controller 80 starts automatic alignment control. Herein, the controller 80 detects misalignment of the photographing part 3 with respect to the examinee's eye based on an imaging signal from the two-dimensional imaging element 65. Further, the controller 80 electronically displays the reticle LT at a predetermined position (a center of the monitor in the present embodiment) on the monitor 8 in correspondence with the photographing optical axis L1. The controller 80 detects an approximate corneal vertex position in the form of the XY coordinate of the center of the ring shape formed by the index images Ma to Mh projected like a ring shape and electronically forms a mark A1 at the corresponding position on the monitor 8. To bring the photographing part 3 in a predetermined positional relationship with the examinee's eye, the controller 80 determines a deviation amount between the alignment reference position (e.g., an intersection point of an imaging plane of the imaging element 65 and the photographing optical axis L1) in the XY direction set in advance on the imaging element 65 and the detected corneal vertex position. The controller 80 then performs the automatic alignment by driving and controlling the XYZ drive part 6 so that the deviation amount falls within a permissible range of alignment completion in the XY direction (so that the reticle LT and the mark A1 coincide with each other).

The controller 80 determines the alignment deviation amount (displacement amount) in the Z direction by comparing the image ratio (a/b) of the image interval "a" between the infinite index images Ma and Me detected as above and the image interval "b" between the finite index images Mh and Mf and the image ratio corresponding to the alignment completion position set in advance in the memory 85. As the alignment completion position in the Z direction (working distance), the controller 80 appropriately retrieves, from the memory 85, a value of the image ratio corresponding to the alignment completion position in the direction corresponding to the deviation amount (displacement amount) in the XY direction of the photographing optical axis L1 from the corneal vertex, and sets this retrieved value as the alignment reference value. In this manner, the controller 80 also determines, regarding the Z direction, the deviation amount from the alignment completion position in the Z direction and then performs the automatic alignment by driving and controlling the XYZ drive part 6 so that the deviation amount falls within the permissible range of the set alignment completion position. Based on the Z-direction alignment deviation amount, the controller 80 electronically displays the indicators G representing the Z-direction alignment state on the right and left sides of the reticle LT displayed on the monitor 8. The number of displayed indicators G is increased or decreased according to the Z-direction alignment deviation amount. In the present embodiment, when the alignment deviation amount in the XYZ direction falls within the permissible range, the controller 80 stops driving the drive part 6 and also outputs an alignment completion signal to display the indicators G, one each on right and left sides (see FIG. 3B).

After completion of alignment with respect to the corneal vertex of the examinee's eye E, the examiner selects a stereo photographing mode by using the switch unit 84. When the stereo photographing mode is established, the controller 80 changes the previously completed alignment reference in the XY direction and sets a new alignment reference position defined as a position apart from the corneal vertex position by a predetermined distance in a horizontal right-left direction (the alignment reference position in only the X direction is changed) in order to obtain a pair of photographing images having a predetermined disparity. The controller 80 further causes the mark A1 to disappear from the monitor 8 and displays a mark A1a corresponding to the new alignment reference. For instance, the mark A1a is displayed in a position assumed to be displaced horizontally by 1 mm to the right from the corneal vertex.

The controller 80 determines the deviation amount between the newly set alignment reference position in the XY direction and the photographing optical axis L1 in a similar manner as above, and starts the automatic alignment by driving and controlling the XYZ drive part 6 so that the deviation amount falls within the permissible range of alignment completion (so that the reticle LT and the mark A1a coincide with each other). FIG. 3C shows a state where the photographing part 3 is in alignment with the new alignment reference position set in the predetermined position in the horizontal direction from the corneal vertex by being moved under the control of the controller 80 based on the newly set alignment reference position in the XY direction in the stereo photographing mode (for convenience, it is regarded that the automatic alignment in the Z direction has not been conducted). The conventional apparatus is configured such that, even when the apparatus is moved only in the horizontal direction while the alignment in the XYZ direction is proper with respect to the corneal vertex of an examinee's eye E, the positions of the alignment indexes Ma and Mh projected to the eye E remain unchanged, and thus the working distance in the Z direction is considered to remain unchanged. In contrast, the present embodiment is configured such that, when the photographing optical axis L1 is deviated from the corneal vertex position, the alignment completion position in the Z direction is changed based on the deviation amount. The controller 80 retrieves, from the memory 85, reference information (herein, the value of the image ratio) assumed as the corresponding alignment completion position in the Z direction based on the detected deviation amount of alignment in the XY direction, and sets a new alignment completion position based on this reference information. In FIG. 3C, while the alignment in the YX direction is in the predetermined permissible range, the alignment in the Z direction is different from the newly set alignment completion position. Therefore, the controller 80 displays the indicators G based on the deviation amount and causes the photographing part 3 to move until a working distance corresponding to the set alignment completion position is obtained. When the alignment deviation amount in the XYZ direction falls within the permissible range, the controller 80 stops driving the drive part 6 and also outputs the alignment completion signal to display the indicators G, one each on right and left sides.

When a changeover switch not shown is used, the controller 80 displays the fundus observation image as shown in FIG. 4 on the monitor 8 and completes focusing by using a split index not shown. In response to a trigger signal generated by use of the photographing switch 4b, the controller 80 removes the dichroic mirror 24 and the flip-up mirror 34 from the optical path and turns on the photographing light source 14 to irradiate flash light to the fundus. Reflection light from the fundus falls on the imaging element 35, and a fundus image is thus obtained. The examiner performs the same operation for an opposite position (in the left direction) apart from the corneal vertex by a predetermined distance to obtain a pair of right and left stereo photographing images.

The above embodiment shows the example that the photographing optical axis is aligned once with the corneal vertex for stereo photographing and then the alignment reference is changed. The invention is, however, not limited thereto. For example, the alignment reference (XY direction) may be originally set in a position displaced by a predetermined amount from the corneal vertex.

The above embodiment exemplifies the stereo photographing but does not limit the invention thereto. The invention is applicable to the photographing performed with the photographing optical axis displaced from the alignment position in the XY direction considered as a normal reference. For instance, as in the peripheral photographing to photograph the peripheral portions of the fundus, when the photographing optical axis is to be aligned with the corneal vertex after the visual line is changed by the fixation target (after the visual line is moved), there is a case where the photographing optical axis is intentionally displaced toward the pupil center in order to avoid illumination unevenness caused when part of the illumination light is eclipsed by an iris. Even in this case, flares are more likely to occur as the displacement amount of the photographing optical axis from the corneal vertex is larger. By changing the working distance based on the displacement amount of the photographing optical axis from the corneal vertex, the occurrence of flares can be prevented. In such peripheral photographing, the eye itself is inclined with respect to the photographing optical axis, and therefore the alignment completion position in the Z direction can also be set in further consideration of such condition. Since this inclination of the eye is determined according to the information of the presenting position of the fixation target, during the peripheral photographing, the alignment completion position in the Z direction may be set by utilizing the information of the alignment deviation amount in the XY direction and the presenting position information.

In addition to the above conditions, a corneal curvature of the examinee's eye may also be taken into consideration. The corneal curvature of the examinee's eye may be determined by use of the aforementioned alignment projecting index(es) or an additional optical system for measuring a corneal curvature. Since it is difficult to measure the corneal curvature while the visual line is moved, the corneal curvature information should be obtained while the examinee's eye faces front.

Still further, the present embodiment exemplifies that the alignment deviation amount in the XY direction is determined with reference to the corneal vertex, but does not limit the invention thereto. As an alternative, the alignment deviation amount of the photographing optical axis may be determined with reference to the pupil center of the examinee's eye.

DESCRIPTION OF THE REFERENCE SIGNS

3 Photographing part
8 Monitor
10 Illumination optical system
30 Fundus observation-photographing optical system
50 Alignment index projecting optical system
60 Anterior-segment observation optical system
70 Fixation target presenting optical system 80 Controller
85 Memory

The invention claimed is:

1. A fundus photographing apparatus for photographing a fundus of an examinee's eye, the apparatus comprising:
   a photographing part including a photographing optical system for photographing the fundus of the eye;
   a moving mechanism for relatively moving the photographing part with respect to the eye;
   a fixation target presenting part for presenting a fixation target to the eye;
   a detecting part for detecting a deviation amount in up and down, right and left directions of a photographing optical axis of the photographing part with respect to a reference position of the eye; and
   an alignment completion position setting part for setting, while a visual line of the examinee's eye is fixed in a predetermined direction by the fixation target presenting part, an alignment completion position in a back and forth direction of the photographing part with respect to the examinee's eye based on the deviation amount in the up and down, right and left directions of the photographing optical axis detected by the detecting part so that the alignment completion position in a back and forth direction is stored as a different value in memory in association with the deviation amount in the up and down, right and left directions.

2. The fundus photographing apparatus according to claim 1, further including an alignment index projecting optical system for projecting an alignment index to the examinee's eye; and
   a light receiving element for receiving the alignment index projected to the eye by the alignment index projecting optical system,
   wherein the detecting part detects the deviation amount in the up and down, right and left directions of the photographing optical axis based on a light receiving signal outputted from the light receiving element.

3. The fundus photographing apparatus according to claim 2,
   wherein the detecting part detects a misalignment amount in the back and forth direction of the photographing part with respect to the examinee's eye based on the light receiving signal outputted from the light receiving element and the alignment completion position set by the alignment completion position setting part, and
   the fundus photographing apparatus further includes a control device for controlling the moving mechanism to move based on the misalignment amount in the back and forth direction obtained by the detecting part or controlling a predetermined indicator to be displayed on the monitor to inform the misalignment amount in the back and forth direction.

4. The fundus photographing apparatus according to claim 1, further including a corneal curvature obtaining part for obtaining a corneal curvature of a cornea of the examinee's eye by use of an index projected to the cornea,
   wherein the alignment completion position setting part uses corneal curvature information of the examinee's eye by the corneal curvature obtaining part to set the alignment completion position in the back and forth direction.

5. The fundus photographing apparatus according to claim 1, wherein the alignment completion position setting part stepwise or continuously changes the alignment completion position in the back and forth direction of the photographing part with respect to the examinee's eye according to the deviation amount in the up and down, right and left directions of the photographing optical axis while a visual line direction of the eye is fixed by the fixation target presenting part.

6. The fundus photographing apparatus according to claim 2, wherein the alignment index projecting optical system projects an infinite alignment index and a finite alignment index to the examinee's eye,
   the detecting part detects a misalignment amount in the back and forth direction of the photographing part with respect to the eye by a ratio between an image of the infinite alignment index and an image of the finite alignment index, and
   the alignment completion position setting part sets the ratio assumed as the alignment completion position based on the deviation amount in the up and down, right and left directions of the photographing optical axis detected by the detecting part to set the alignment completion position in the back and forth direction of the photographing part with respect to the eye.

7. The fundus photographing apparatus according to claim 6, further including a storage part that stores a plurality of the ratios assumed as the alignment completion position according to the deviation amount in the up and down, right and left directions of the photographing optical axis.

* * * * *